(12) United States Patent
Kulp, III et al.

(10) Patent No.: US 8,975,368 B2
(45) Date of Patent: Mar. 10, 2015

(54) METHODS FOR PREPARING LINKED PEPTIDE RINGS AND PEPTIDE NANOTUBES OBTAINED THEREBY

(75) Inventors: John L. Kulp, III, Alexandria, VA (US); Manoj K. Kolel-Veetil, Alexandria, VA (US); Thomas D. Clark, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 765 days.

(21) Appl. No.: 12/855,379

(22) Filed: Aug. 12, 2010

(65) Prior Publication Data

US 2011/0046345 A1 Feb. 24, 2011

Related U.S. Application Data

(60) Provisional application No. 61/233,563, filed on Aug. 13, 2009.

(51) Int. Cl.
*B82Y 5/00* (2011.01)
*B82Y 30/00* (2011.01)
*B82Y 40/00* (2011.01)
*C07K 7/50* (2006.01)
*C07K 7/64* (2006.01)
*A61K 38/00* (2006.01)
*A61K 38/12* (2006.01)

(52) U.S. Cl.
CPC ... *B82Y 5/00* (2013.01); *C07K 7/50* (2013.01); *A61K 38/00* (2013.01); *A61K 38/12* (2013.01); *C07K 7/64* (2013.01); *B82Y 30/00* (2013.01); *B82Y 40/00* (2013.01)
USPC ............ 530/317; 530/332; 514/21.1

(58) Field of Classification Search
None
See application file for complete search history.

(56) References Cited

U.S. PATENT DOCUMENTS

| 6,613,875 B1 | 9/2003 | Ghadiri |
| 6,902,720 B2 | 6/2005 | McGimpsey |
| 2005/0107289 A1 | 5/2005 | Ghadiri et al. |

OTHER PUBLICATIONS

Xie, H. et al. J. Mater. Chem. (2005); 15; pp. 1734-1741.*
Block et al. *Top. Curr. Chem.* 245:89-150 (2005).
Bong, D.T. et al. Angew. Chem. Int. Ed. 2001, 40, 988.
Clark et al. *Chem. Eur. J.* 5:782-792, (1999).
Clark et al., J. Am. Chem. Soc. 117:12364-12365 (1995).
Fujimura et al. *Org. Lett.* 9:793-796 (2007).
Gazit, E., Chem. Soc. Rev. 2007, 36, 1263.
Ghadiri et al. *Nature* 366:324-327 (1993).
Hartgerink *Curr. Opin. Chem. Biol.* 8:604-609 (2004).
Hirata et al. *Biopolymers* 88:150-156 (2007).
Martyna G.J. et al., J. Chem. Phys. 1999, 110, 2810.
Osapay et al. *J. Am. Chem. Soc.* 112:6046-6051 (1990).
Podlech et al., *Liebigs Ann*.1217-1228 (1995).
Seebach et al. *Chem. Commun.* 2015-2022 (1997).
Seebach et al. *Helv. Chim. Acta* 80:173-182 (1997).
Vollmer et al. *Angew. Chem. Int. Ed.* 38:1598-1601 (1999).

* cited by examiner

*Primary Examiner* — Kevin S Orwig
(74) *Attorney, Agent, or Firm* — US Naval Research Laboratory; Roy Roberts (57) ABSTRACT

Peptide nanotube polymers and methods of making such are disclosed. The peptide nanotube polymers are comprised of alternating monomers of the first peptide ring and monomers of the second peptide ring covalently bonded to one another via a linker, and can be functionalized. The described peptide nanotube polymers can enjoy the combined properties of healing and toughness, self-reporting, and tunability and actuation.

10 Claims, 7 Drawing Sheets
(6 of 7 Drawing Sheet(s) Filed in Color)

PRIOR ART

METHODS FOR PREPARING LINKED PEPTIDE RINGS AND PEPTIDE NANOTUBES OBTAINED THEREBY

CROSS-REFERENCE TO RELATED APPLICATIONS

This Application claims the benefit of U.S. Provisional Application 61/233,563 filed on Jul. 31, 2009, which is incorporated herein by reference.

BACKGROUND

Natural biological materials provide numerous functional nanostructures and attractive materials. Proteins and peptides represent a fundamental fraction of natural biological molecules that carry out a host of essential functions in biology, including molecular recognition, catalysis, information storage, and controlled crystallization of inorganic materials.

Figure 1:
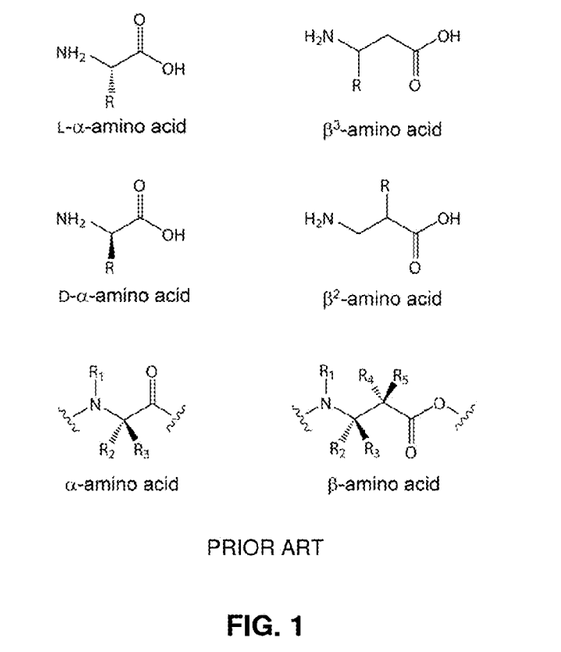
FIG. 1 illustrates common nomenclature for α-amino acids and β-amino acids with possible substitution and isomeric configurations.
Figure 2:
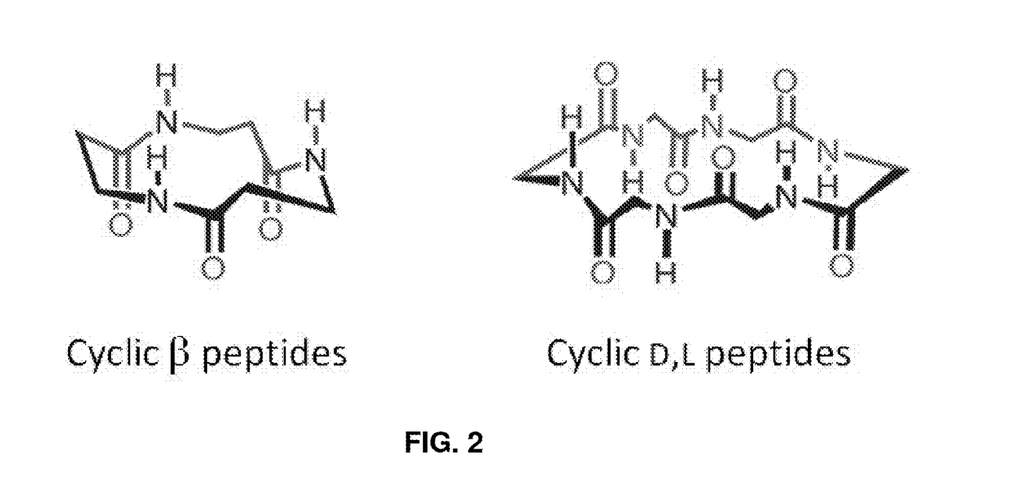
FIG. 2 illustrates the minimum structures for flat rings shown for D,L peptides and β peptides.

Amino acids are the molecular building blocks of peptides and proteins. An amino acid contains both an amine group and a carboxyl group separated by a single carbon atom termed the α carbon. Attached to the α carbon is an organic substituent, the side chain. Of the natural 20 amino acids, 19 have a chiral α carbon, with the most common chirality being L; however, D amino acids are also found. Alternatively, chiral centers are defined using the R,S system. For α-amino acids, there are two possible R,S configurations and three potential sites for substitution, seen in FIG. 1. Unlike α-amino acids, β-amino acids contain two carbon atoms between the amine group and the carboxyl group. If a side chain bonds to the carbon closest to the amino group, the β-amino acid is termed a $\beta^3$-amino acid. Similarly, if the side chain bonds to the carbon closest to the carboxyl group, then the amino acid is termed a $\beta^2$-amino acid. For β-amino acids, there are eight possible R,S configurations and five possible sites for substitution. Various amino acids are illustrated in FIG. 1. It is readily apparent that the possible number of isomers increases significantly from the α-amino acid to the β-amino acid.

In 1993, researchers published the design, synthesis, and characterization of cyclic D,L peptides that self assemble into hollow tube-like structures as confirmed by electron microscopy and electron diffraction (Ghadiri et al. *Nature* 366:324-327 (1993)). By 1995, the Ghadiri group showed that the peptide rings can be covalently linked, thus trapping the dimeric form (Clark et al., *JACS* 117:12364-12365 (1995)). The authors expanded on this work demonstrating that dimers can be formed using photoswitchable linkers, where the linker is composed of an azobenzene subunit that leads to a reversible E to Z photoisomerization (Vollmer et al. *Angew. Chem. Int. Ed.* 38:1598-1601 (1999)). The authors note that the E isomer of the azobenzene exists as a diverse group of oligomers, formed as a result of the intermolecular hydrogen bonding between dimers, yet only a dimer pair is covalently linked. Again in 1999, the same group showed that the dimers can be created using iodine oxidation of cysteine residue in the monomers to form disulfide bonds or by using an olefin metathesis reaction involving the monomers to form a solely carbon-based linker between them (Clark et al. *Chem. Eur. J.* 5:782-792). These linked dimers are not inhibited by the kinetic instability of the non-covalently linked system and show some kinetic and thermodynamic stabilities. Non-linked cyclic peptide tubes are disclosed by Ghadiri for producing D,L peptide subunits (U.S. Pat. No. 6,613,875) and α-amino acids that have a repeating D,L unit or homochiral β-amino acids for use as antimicrobial peptides and compositions (U.S. patent application number US 2005/0107289).

Tubular assemblies of β-peptide rings are similar in fashion to those of α-peptides described by Ghadiri. Seebach et al. found that cyclic tetramers of 3-aminobutanoic acid exhibited X-ray powder diffraction patterns showing tubular crystal packing with nonlinear hydrogen bonding (Seebach et al. *Helv. Chim. Acta* 80:173-182 (1997)). The Kimura group synthesized a cyclic tri-β-peptide with trans-2-aminocyclohexylcarboxylic acid residues that self assembled into a rod-shaped molecular assembly (Fujimura et al. *Org. Biomol. Chem.* 4:1896-1901 (2006)). In 2007, Kimura demonstrated that the tube-like molecular assemblies can form from cyclic hexa-β-peptides (Hirata et al. *Biopolymers* 88:150-156 (2007)). The same group reported a cyclic tri-β-peptide system that contained terpyridine metal ligands that self assembled into tubes (Fujimura et al. *Org. Lett.* 9:793-796 (2007)). The terpyridine ligands bound the Cu(II) ions without disruption to the tubular assembly. McGimpsey disclosed cyclic D,L peptides and β peptides comprising of chromophore residues which possess electronic and electro-optic properties for the production of such devices (U.S. Pat. No. 6,902,720).

As best as can be determined, no prior research group has been able to link more than two peptide rings, due to the synthetic and structural complexity of the system. It appears that research on assemblies of peptide rings has been limited to noncovalent tube-like structures and linked dimer structures. It should be clear to one of skill in the art that a linked polymeric ring system would have enhanced properties when compared to an unlinked system.

With the aim to facilitate the use of the linked peptide scaffold as a tool in bionanotechnology, a method to produce peptide nanotubes polymers is presented. This disclosure describes a new method of covalently linking peptide rings in a way that prevents dimerization and allows for polymerization of the rings. This invention has implications not only in peptide and protein chemistries but also in the discovery and development of novel smart materials that are expected to show a number of enhanced properties when compared to natural biological systems.

BRIEF SUMMARY

In one embodiment, method of preparing a peptide nanotube polymer comprises (a) providing a plurality of a first peptide ring and a plurality of a second peptide ring, and (b) polymerizing the first peptide rings and the second peptide rings to produce a peptide nanotube polymer, wherein the peptide nanotube polymer comprises alternating monomers of the first peptide ring and monomers of the second peptide ring covalently bonded to one another via a linker via a linker formed during the polymerization, and wherein the peptide rings are arranged such that an exterior surface of the peptide nanotube polymer corresponds to exteriors of the first and second peptide rings.

Optionally, the first peptide ring and the second peptide ring are the same prior to and/or after polymerization. In another embodiment, the first peptide ring and the second peptide ring are different from one another prior to and/or after polymerization.

In another embodiment, method of preparing a peptide nanotube polymer comprises (a) providing a plurality of a first peptide ring and a plurality of a second peptide ring, wherein the first peptide ring and second peptide ring are each β-peptides comprising three amino acids, and (b) polymerizing the first peptide rings and the second peptide rings to produce a peptide nanotube polymer, wherein the peptide nanotube polymer comprises alternating monomers of the first peptide ring and monomers of the second peptide ring covalently bonded to one another via a linker via a linker formed during the polymerization, wherein the peptide rings are arranged such that an exterior surface of the peptide nanotube polymer corresponds to exteriors of the first and second peptide rings, and wherein, before said polymerizing, the first peptide ring comprises at least one primary amine and the second peptide ring comprises at least one carboxylic acid, and wherein said linker comprises at least one an amide bond created from the at least one amine and the at least one carboxylic acid during polymerization.

In still another embodiment, a peptide nanotube polymer comprising alternating monomers of a first peptide ring and monomers of a second peptide ring covalently bonded to one another via a linker having a length of from 6 to 10 atoms, wherein the peptide rings are arranged such that an exterior surface of the peptide nanotube polymer corresponds to exteriors of the first and second peptide rings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3(a) is a drawing depicting the cyclic β tripeptide monomers. FIG. 3(b) is a schematic representation of a monomer ring. FIG. 3(c) is a sketch illustrating the monomer ring modified with two carboxylic acid functionalities. FIG. 3(d) is a sketch illustrating the monomer ring with two primary amine functionalities. FIG. 3(e) shows the stacked nanotube structure after polymerization of monomer rings in FIGS. 3(c) and (d), rings shown in black/gray and linker shown in red. FIG. 3(f) is a schematic representation of the polymerized structure.

FIG. 4(a) shows density functional theory (DFT) calculations of the binding energy per monomer ring, up to 8 rings. The exact energies are shown above the number of monomer rings. FIG. 4(b) shows the binding energy (red) and dipole moment per monomer (blue) as a function of length.

FIG. 6(a) illustrates that, under basic conditions, the amine is neutral and the dimer formation is favorable. FIG. 6(b) illustrates that, under neutral or acidic conditions, the amine is protonated and the dimer formation is energetically unfavorable.

FIG. 8(a) shows amine side chains expected to provide pH-induced actuation. FIG. 8(b) illustrates optical functions. FIG. 8(c) shows how the PNP undergoes a conformational change in response to external stimuli such as light. FIG. 8(d) illustrates how electronic capabilities can also be designed into the PNPs.

DETAILED DESCRIPTION

Definitions

As used herein, the term "and/or" with reference to two or more items refers to any combination of one or more of the items.

As used herein, reference to a numerical size of a ring refers to the number of atoms in the ring itself, exclusive of the atoms attached to the ring.

As used herein, the term "peptide nanotube polymer" refers to a polymer comprising at least three linked peptide rings.

Linked Peptide Rings

The desire to mimic biological material functions has inspired the field of smart materials, which includes materials whose properties are controlled with external stimuli. The inspiration to make materials with these properties comes from biological proteins.

One example of a natural material having desirable material properties is the mechanical protein titin, which exemplifies the property of healing and toughness. The modular structure of titin allows linkage of many monomeric units together using a combination of weak, reversible bonds and strong, permanent bonds that hold the molecule together, so that when titin is stretched, the individual modules unfold through the breaking of the weak bonds, but when titin is released it snaps back into its original shape because the strong bonds remain intact.

Looking to biology for inspiration, proteins—such as titin—exist that have only a subset of the desired properties. One potential way to achieve a molecule having all of the desired properties is to try to modify a natural protein. However, such an approach is dangerous because tinkering with an existing protein can often destroy the good properties that one wishes to preserve. Described herein is an alternate strategy: to abstract principles from biology, in this case the modularity and combination of weak and strong bonds found in titin, and to design a synthetic system that has the healing and toughness found in titin and that can be easily modified to have the additional properties of self-reporting and tunabilty and actuation.

Cyclic peptides embody a large division of natural and synthetic compounds that exemplify some of the desired properties. Synthetic cyclic peptides are formed by the cyclization of either alternating D-,L-α-amino acids (D,L peptides) or β-amino acids (β-peptides). The minimal structure to obtain a flat, ring-shaped structure required for assembly is 6 amino acids for D,L peptides and 3 amino acids for β-peptides. When cyclic peptides have too many amino acids, the larger size causes deformation of flat ring structure, thus preventing ring assembly. Preferably, the peptide ring has a size of 6 to 12 amino acids in the case of a peptides or a size of 3 to 8 amino acids in the case of β peptides. Another restriction on the use of D,L peptides is the requirement of using alternating D and L amino acids, so the repeat unit is a two amino acid D,L unit. Preferred ring sizes for assembly include ring sizes of 6, 8, 10, and 12.

Described herein is a new method of linking cyclic peptide monomers into polymers, such polymers being termed peptide nanotube polymers (PNPs). Peptide rings have a stable flat, disk-like conformation with the amino acid side chains pointing to the outside of the ring. These disks can assemble, through hydrogen bonding, into nanoscale tubes. Any disruption to the stabilizing hydrogen bonding causes disassembly of the tube structure. Although reassembly is possible, the sequential order of the disks is not reliably recovered, and this sequential order can be required in order for the material to enjoy certain properties. The described method links the rings so that if the resulting tube structure is disrupted, the linking will prevent the rings from full disassembly, thus allowing the original tube structure to be reformed. This trait exemplifies a property of healing and toughness: the ability of a material to undergo a mechanical deformation when subjected to a stress and return to its original state when the stress is removed. Embodiments of the described PNPs are self-reporting, i.e., sensitive to the mechanical state or environment such that a detectable change in its optical or electronic property is provided in response to an external stimulus. The linked nanotubes are also capable of tunability and actuation, that is, changes in properties induced by external stimuli. Methods of preparing and using such PNPs are presented, which can provide superior ability in the control and function of cyclic peptide tubes. PNPs, in one molecule, show all of these properties: (i) healing and toughness, (ii) self-reporting, and (iii) tunability and actuation. The present disclosure may be advantageously applied to bottom-up approaches in bionanotechnology, as well as in applications including, but not limited to, coatings, sensors, ion channels, electronics, and catalysis.

Figure 3:
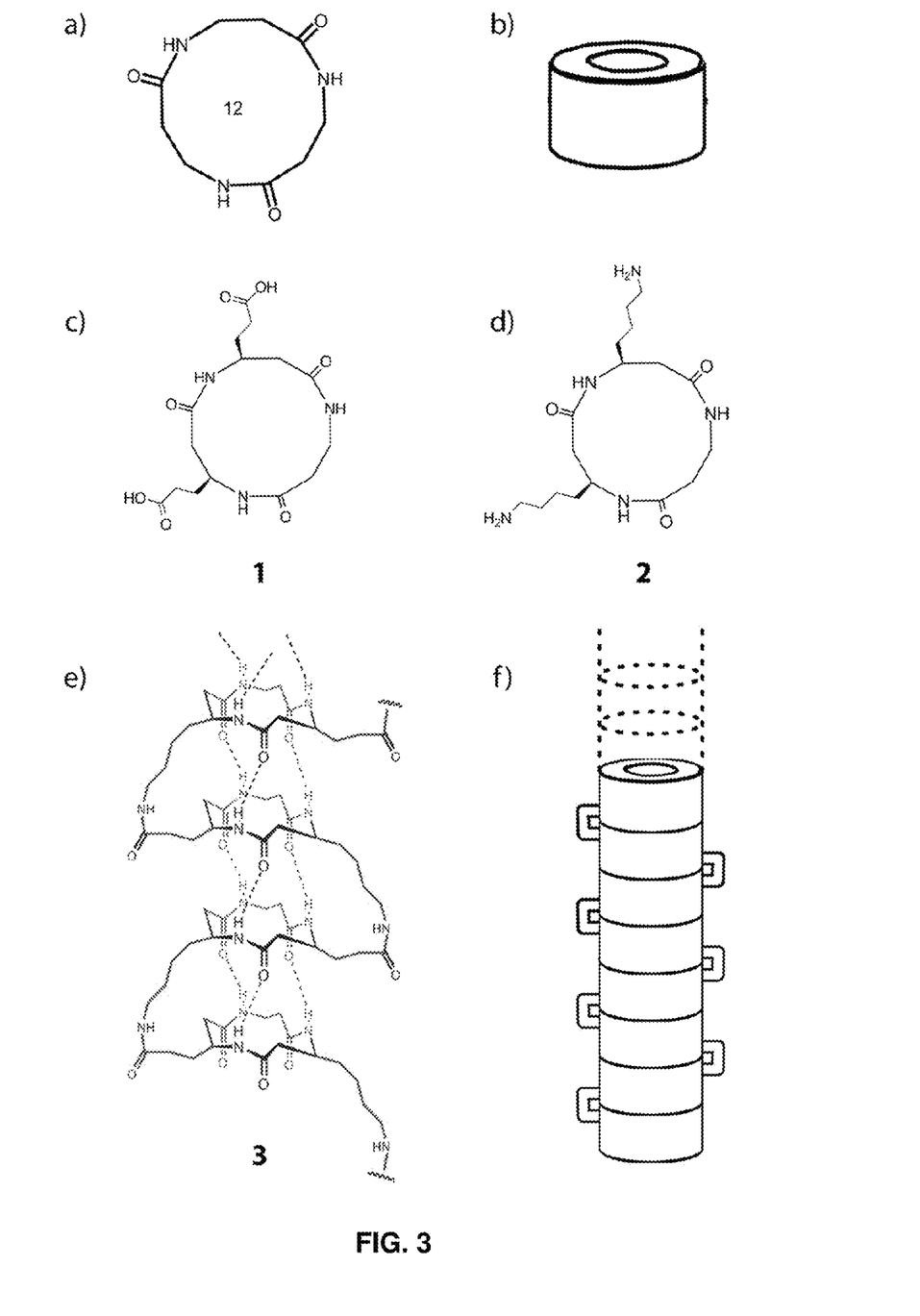
FIG. 3 is a schematic diagram showing one possible nanotube assembly from cyclic β tripeptide monomers.

It was initially decided to pursue PNPs based on β peptides instead of D,L-α-peptides; β-peptide rings stack through hydrogen bonding of the backbone amide group and all of the amide bonds point in one direction, which will give the resulting nanotubes structure an overall dipole moment. This large dipole moment could have possible applications in molecular devices (Fujimura et al. *Org. Lett.* 9:793-796 (2007)). An illustrative cyclic β tripeptide ring being synthesized consists of three β-amino acids and three linking amide bonds giving a twelve membered ring as seen in FIG. 3(*a*). FIG. 3(*b*) is a schematic representation of a monomer ring. Ring 1 has two carboxylic acid functionalities, as seen in FIG. 3(*c*): one for connecting to the ring above, and one for connecting to the ring below. Similarly, ring 2 (FIG. 3(*d*)) has two primary amines that are intended to react with the carboxylic acids to form amide bonds, thus linking to a ring above and a ring below it. The illustrated embodiment has the monomeric rings joined with an amide linker, as seen in FIG. 3(*e*). Reference numeral 3 therein depicts four monomeric rings joined by amide linkers. These linkers or "hinges" work to prevent the rings from undesirably dissociating, for example during actuation by external stimuli. The linkers can take any suitable form including, but not limited to, carbon atoms, azobenzene functionalities, thioether bonds, lactone bridges, and other typical linkers, and/or combinations thereof familiar to one of skill in the art.

Figure 4:
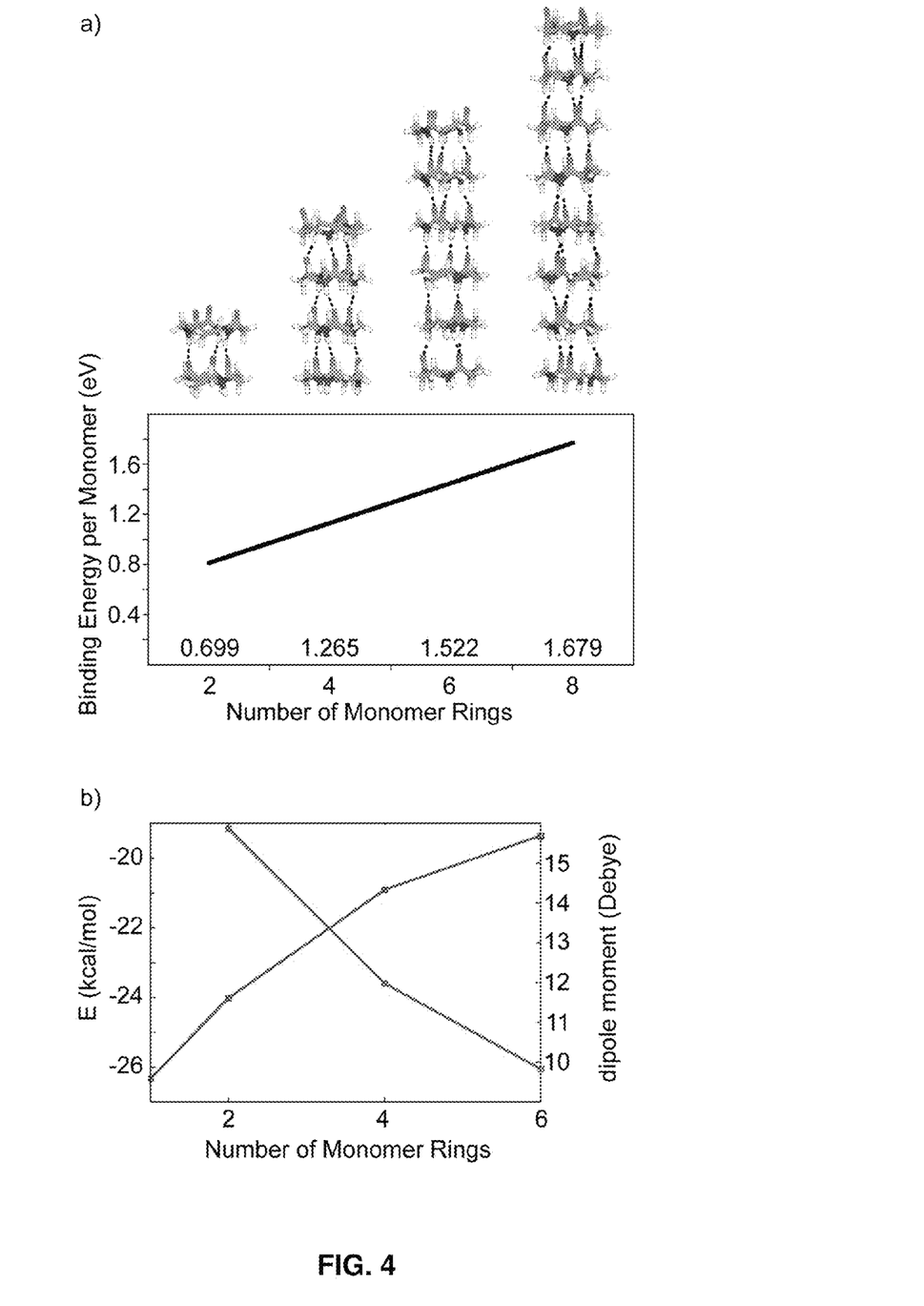
FIG. 4 shows calculated binding energy.

The binding of one to eight ring monomers without the side-chain cross-linkers was simulated, with the results shown in FIG. 4. The dimer binding energy is about 19 kcal/mol, and increases almost linearly for additional monomers. The dipole moment per monomer of the dimer is about nine Debye, and also increases nearly linearly with additional monomer binding. These observations are consistent with inter-monomer binding caused by a combination of hydrogen bonds, three per ring, and an electrostatic interaction of the monomer dipole with the combined dipoles of the monomers in the rest of the peptide nanotube. As the tube length increases, its dipole increases, leading to increased electrostatic energy gain for and during further addition of monomers. It is expected that the increase in dipole and binding energy will end once the electric field created by the tube dipole is strong enough to create a charged defect or cause an electron transfer at one end of the tube.

The PNPs as described herein preferably comprise at least 3 or more monomers, for example 3, 4, 5, 6, 7, 8, 9, 10, 11, 12, or more monomers.

Figure 5:
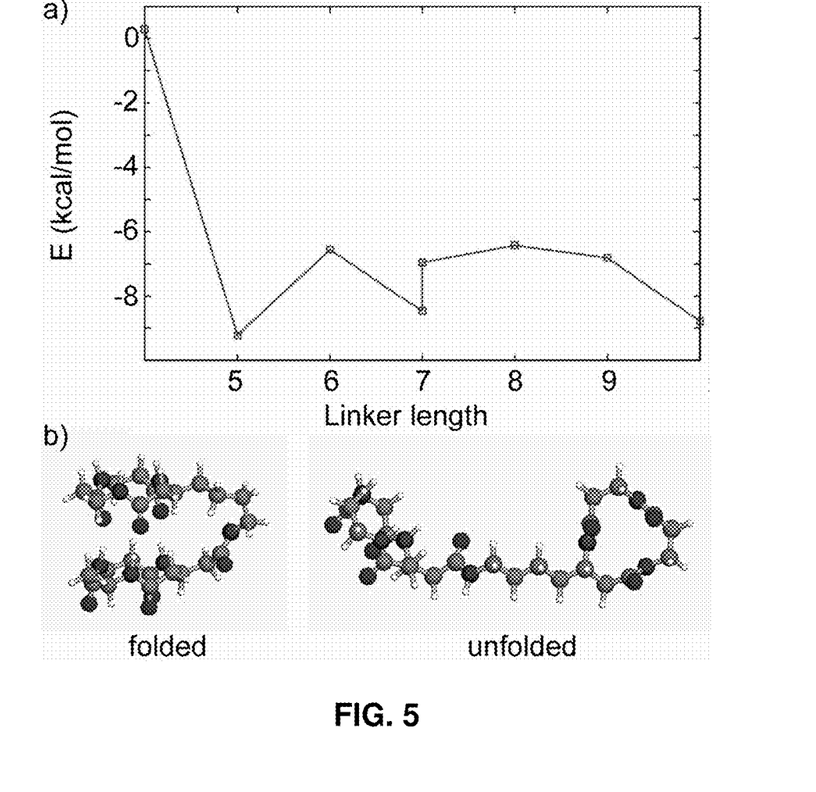
FIG. 5(a) is a plot of the folding energy versus linker lengths from DFT calculations, Energy=E(folded)−E(unfolded). The two data points at a linker length of 7 are derived from two different unfolded conformations and can be interpreted as an error bar.
FIG. 5(b) shows molecular models showing the folded and unfolded conformations.

Using density functional theory (DFT), the folding energy was computed for a dimer composed of two monomers connected by covalently bonded side chains of various lengths (FIG. 5). The folding energy is somewhat smaller than the binding energy for the non-cross-linked monomers, and approximately independent of cross-linker length above a critical minimum length. The shortest cross-linker, the 4 atom linker, fully satisfying the hydrogen bonds criterion causes strain in the monomers and side chain, and makes the folding energetically unfavorable. Linker-length calculations were also performed using molecular dynamics. The molecular dynamics simulations were conducted using a "MM+force field"—the simulations started with a folded conformation and proceeded at constant temperature for 100 ps. The linker with 4 atoms completely unfolded, while linkers with 6, 8, or 10 atoms remained folded during the simulation. For the 6 atom linker, the hydrogen bond furthest from the linker elongates although it does not fully break during the simulation. The shortest linker examined was 4 atoms; the DFT and force-field MD results are consistent suggesting that a 4 atom linker is unfavorable. From these data, it was decided to pursue the 8 atom linker for effecting polymerization in the illustrated example. However, it should be clear to one of skill in the art that the appropriate linker length can vary depending on the nature of the polymerized cyclic peptide monomer/s, including the ring size.

Figure 6:
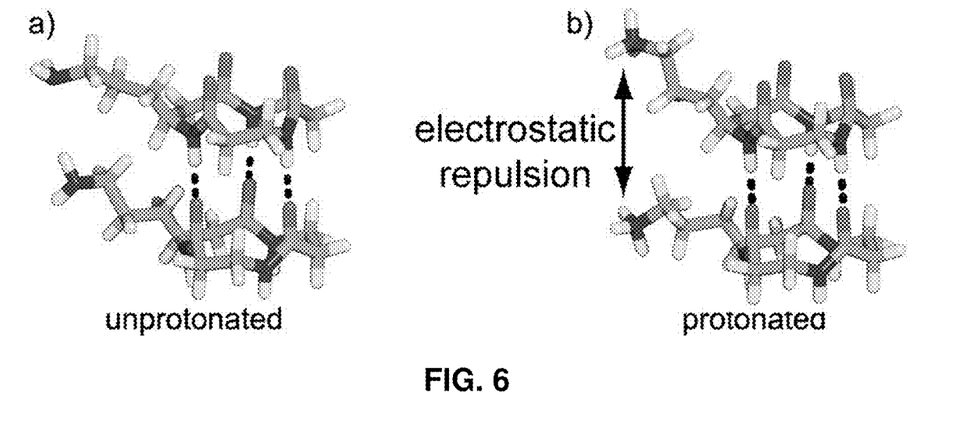
FIG. 6 shows non-linked dimers with primary amine group that is responsive to external stimuli such as pH.
Figure 7:
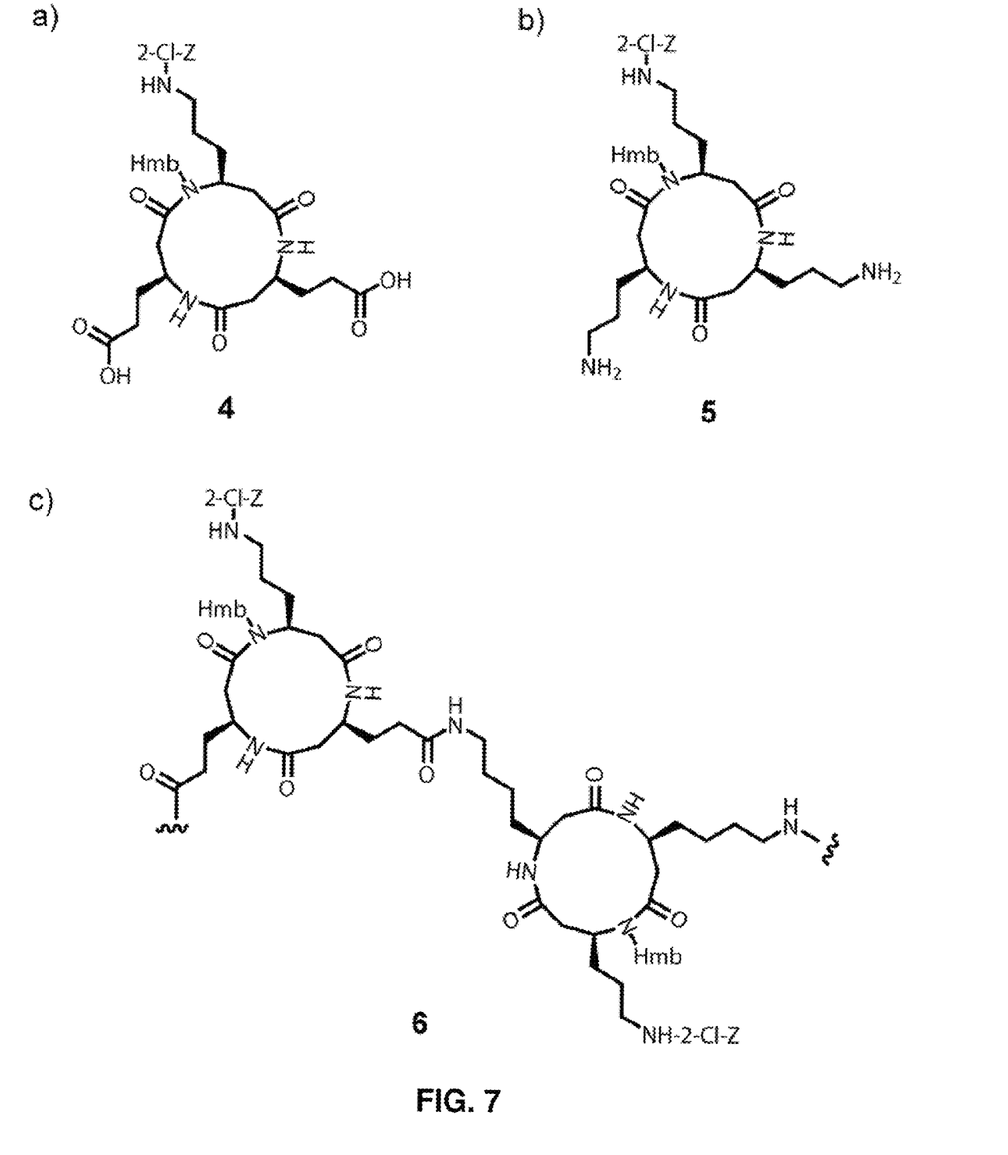
FIG. 7 is a chemical representation of some of the synthesized ring structures.

To actuate folding/unfolding, the effect of protonation was examined on a non-linked dimer (FIG. 6), where the binding energy was compared between dimers of neutral and protonated monomers. The neutral dimer had an approximate binding energy of −16 kcal/mol, exhibiting a favorable stacking of the two monomers. The protonated dimer had an estimated binding energy of 23 kcal/mol, suggesting that the protonated dimer does not bind at all. Electrostatic modulation via pH change appears to be a facile method to control the folding/unfolding, and thus to control the length of this type of polymer. It is expected that the elongation of the polymer may be monitored by circular dichroism, wherein the folded and unfolded conformations provide distinctive bands. In this sense, the polymer self-reporting provides a simple and direct measure of its local chemical environment.

β-amino acids are depicted in FIG. 7. Synthesis of β-amino acids was performed as described previously (Podlech and Seebach *Liebigs Ann.* 1217-1228 (1995)). Ring 4 has two carboxylic acid functionalities (FIG. 7(*a*)): one for connecting to the ring above, and one for connecting to the ring below. Similarly, ring 5 (FIG. 7(*b*)) has two primary amines that are intended to react with the carboxylic acids to form amide bonds, thus linking to a ring above and a ring below it. In our illustrative case, the linking results in an amide bond, which can form under a variety of conditions where the carboxyl group is usually activated often using carbodiimides and triazoles. The polymerization reaction could likely result in dimerization. To prevent dimerization and promote polymerization, it was decided to incorporate a hydroxymethyl benzoate (Hmb) protecting group on the nitrogen of the nonlinking residue (FIG. 7(c)). This protecting group prevents the rings from fully hydrogen bonding with each other and thus facilitating the linking reaction to occur linearly among the rings. After polymerization, deprotection of the Hmb protecting group frees up the amide group to support hydrogen bonding and nanotube assembly. However, it should be clear to one of skill in the art that a protection strategy using the Hmb group may be completely unnecessary in the cases of rings where polymerization is favored over dimerization. It should also be clear to one of skill in the art that protection by the Hmb group is but one of several strategies that are available for preventing such dimerization between rings. We note that removing the Hmb will not hinder the synthesis of the ring structure, and we are also pursuing this strategy to determine if the Hmb protection is necessary.

It is expected that one of ordinary skill in the art can perform polymerization of the monomer peptide rings to obtain the described nanotubes without undue experimentation. Such polymerization can be attempted at various concentrations of the participating rings to arrive at the optimum monomer concentrations that will lead to the production of a polymeric nanotube structure rather than a dimer structure. Such studies, in addition to the optional use of a polymerization-promoting agent such as the Hmb group, should facilitate the production of PNPs of desired lengths. Once the optimum reaction concentrations have been determined, the extent of reaction and degree of polymerization can be calculated using the well-known Carothers equation taking into account the fact that the number of reactive functionalities in the two participating rings is the same.

These β-peptide rings have 3 amino acids. Each β-amino acid has 5 possible points of attachment (see FIG. 1). In this case only a singular function, one side chain, was added to each amino acid although many other possible combinations exist for placement of linkers and other functionalities. Two of the ring amino acids are for (i) linking to the ring above and (ii) linking to the ring below, which leaves one amino acid that does not participate in the linking. For this position, it was decided to incorporate an ornithine residue (FIG. 6) in the illustrative example. After deprotection of the 2-Cl-Z group, a primary amine functionality will be present. Other functionalities can be introduced, on all R sites shown in FIG. 1 (β-amino acid), so long as the ring maintains two linker functionalities, one for linking the ring above and one for linking the ring below.

Figure 8:
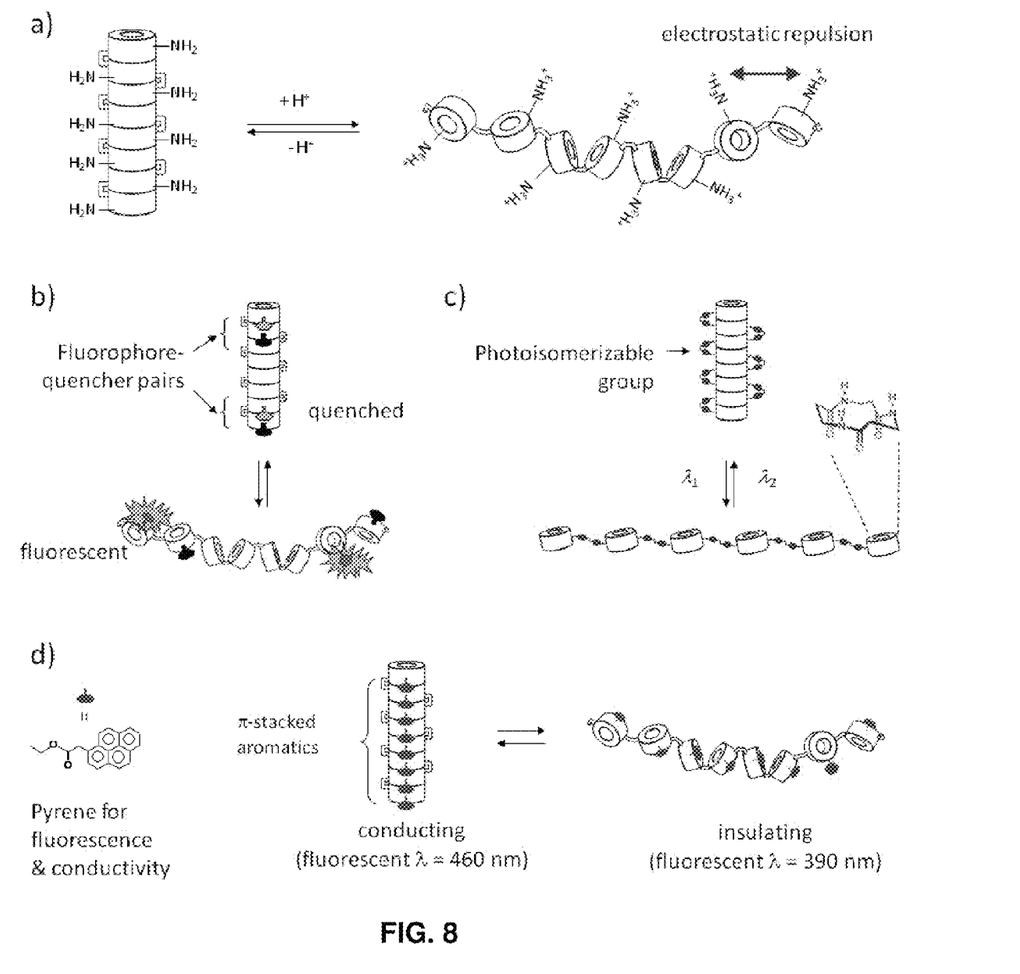
FIG. 8 shows various prophetic embodiments of the described peptide nanotube polymers ("PNPs").

The disclosed linked peptide rings can potentially function in many ways, some of which are illustrated in FIG. 8. The amine groups can induce conformational changes in response to external stimuli such as pH, seen in FIG. 8(a). When the pH of the environment is low, the amine groups are deprotonated and stacking is favorable. When the pH is high, the groups are positively charged and repel each other. It is possible to attach fluorophore-quencher pairs as in FIG. 8(b) so that when the rings in a PNP stack, the fluorescence is quenched, and yet when the stacking is stressed or disassembled, the groups fluoresce. Instead of using an amide bond to link the rings, it is possible to use photoswitchable linkers, where the linker is composed of an azobenzene subunit (FIG. 8c). Here, light is the external stimulus that causes a conformational change. Using the free amine group, one could attach a pyrene unit that conducts when the PNPs stack and insulates when the PNPs unfold (FIG. 8(d)). Numerous other possible applications exist that utilize the folding-unfolding process of the PNPs.

Figure 9:
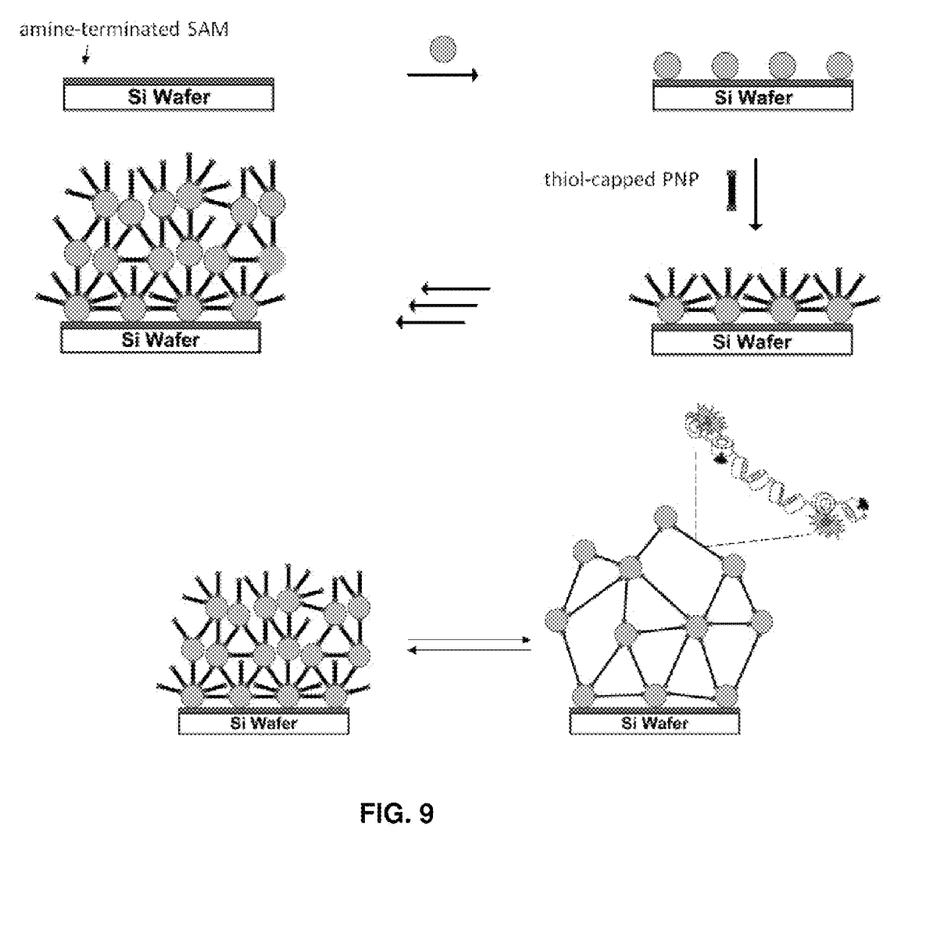
FIG. 9 shows how a layer-by-layer self-assembly of the described PNPs exploits a simple anisotropic architecture.

Instead of functionalizing the subunits along the PNP chain, they can be functionalized at their ends. One embodiment of such functionalization is seen in FIG. 9. This could allow for preparation of layered composites of PNPs and nanoparticles. Such composites could allow for the testing of some of the expected mechanical, electronic, and optical properties on a micro-to-macroscopic scale. Furthermore, more ordered composite materials using transition-metal director complexes could be produced.

The method described herein provides a novel procedure for preparing peptide nanotube polymers (PNPs). This method provides many advantages:

1. PNPs are preferably modular and combine weak and strong bonds. In contrast, previous peptide nanotubes contained ring subunits that interacted and stacked only through weak bonds that could easily be disrupted causing the loss of structure and possibly of function. The disclosed peptide scaffold utilizes covalent (strong) and noncovalent (weak) bonds to link the peptide rings. This combination allows the nanotubes to unfold and refold with the same ring sequence intact.
2. The cooperativity between the covalent bonds and the weak bonds prevents the PNPs from disassembly and supports facile reassembly, which is a unique feature not found in other peptide nanotubes structures.
3. The linkages and corresponding peptide rings are nanostructures amenable to nanomaterials. PNPs provide a distinct three-dimensional architecture where the tube length can be interrogated and controlled with external stresses or stimuli, but the tubes do not fully disassemble.
4. PNPs combine the properties of healing and toughness, self-reporting, and tunability and actuation. Healing and toughness is the ability of a material to undergo a mechanical deformation when subjected to a stress and return to its original state when the stress is removed. Self-reporting is the change in properties in response to an external stimulus, and tunability and actuation is the capability to control the properties of the material through external stimuli. Looking to biology, there are proteins with one of the three properties, but never all three of these properties without modification.
5. The ring subunit of the PNPs is small and chemically accessible. Functionalization of a natural protein is difficult and often affects the structure, which commonly spoils the native and intended properties. In our scaffold, each β-amino acid is easily synthesized and has five possible points of functionalization. Using β peptide rings of eight amino acids gives up to forty attachment points, with two being reserved for the linking. As a result of the synthetic accessibility, PNPs have clear functional advantages over modification of natural proteins.

Alternatives to the peptide ring structure are cyclic D,L peptides (Ghadiri et al. *Nature* 366:324-327 (1993)), mixed α, β peptides (Seebach et al. *Chem Commun* 2015-2022 (1997)), or any other type of flat disk-like molecule that has the ability to form weak bonds with the flanking ring above and below. Alternatives to the linker have been listed in the background information and include, although are not limited to, disulfide bonds (Clark et al. *Chem. Eur. J.* 5:782-792 (1995)), azobenzene subunits (Vollmer et al. *Angew. Chem. Int. Ed.* 38:1598-1601 (1999)), hydrocarbon chains (Clark et al., *JACS* 117:12364-12365 (1995)), lactam bridges (Osapay et al. *JACS* 112:6046-6051 (1990)), and potentially any other type of covalent linkage known to one of skill in the art.

Each and every document cited in this disclosure is incorporated by reference in its entirety.

All numbers expressing quantities of ingredients, constituents, reaction conditions, and so forth used in the specification are to be understood as being modified in all instances by the term "about." Notwithstanding that the numerical ranges and parameters set forth, the broad scope of the subject matter presented herein are approximations, the numerical values set forth are indicated as precisely as possible. Any numerical value, however, may inherently contain certain errors resulting, for example, from their respective measurement techniques, as evidenced by standard deviations associated therewith.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed in accordance with 35 U.S.C. §112, ¶6 unless the term "means" is expressly used in association therewith.

What is claimed is:

1. A method of preparing a peptide nanotube polymer, the method comprising:
   (a) providing a plurality of a first peptide ring comprising two carboxylic acid functionalities and a plurality of a second peptide ring comprising two primary amine functionalities, wherein each of the first and second peptide rings comprises a protecting group on an amide nitrogen in the ring configured to inhibit hydrogen bonding between the rings;
   (b) polymerizing the first peptide rings and the second peptide rings to produce a peptide nanotube polymer; and
   (c) deprotecting the protecting groups after the polymerizing,
   wherein the peptide nanotube polymer comprises alternating monomers of the first peptide ring and monomers of the second peptide ring covalently bonded to one another via a linker having a length of from 6 to 10 atoms and comprising at least one amide bond formed during the polymerization, and
   wherein the peptide rings are arranged such that an exterior surface of the peptide nanotube polymer corresponds to exteriors of the first and second peptide rings.

2. The method of claim 1, wherein the protecting group on the amide nitrogens in each of the rings is hydroxymethyl benzoate.

3. The method of claim 1, wherein adjacent monomers are covalently bonded to one another via at least two linkers.

4. The method of claim 1, wherein the first and second peptide rings comprise D,L peptides or β-peptides and, have a size of 6 to 12 amino acids in the case of D,L peptides or a size of 3 to 8 amino acids in the case of β peptides.

5. The method of claim 1, wherein the first and second peptide rings comprise β-peptides comprising three to eight amino acids.

6. The method of claim 1, wherein the first peptide rings and/or the second peptide rings are functionalized with:
   (a) free amine;
   (b) free acid;
   (c) fluorophore/quencher pairs;
   (d) thiol;
   (e) insulating moiety;
   (f) alkyne;
   (g) photoisomerizable groups;
   (h) aryl- or vinyl-halide;
   (i) alkene;
   (j) azide;
   (k) conducting moiety;
   (l) multiply-bonded transition metals;
   (m) pyrene;
   (n) aryl- or vinyl-boronic acid; or
   (o) isocyanates.

7. The method of claim 1, further comprising protecting at least some of the carboxylic acid functionalities and primary amine functionalities with protecting groups prior to polymerization.

8. The method of claim 1, wherein the peptide nanotube polymer comprises at least four peptide rings.

9. A method of preparing a peptide nanotube polymer, the method comprising:
   (a) providing a plurality of a first peptide ring comprising two carboxylic acid functionalities and a plurality of a second peptide ring comprising two primary amine functionalities, wherein the first peptide ring and second peptide ring are each β-peptides comprising three to eight amino acids comprising a protecting group on an amide nitrogen in the ring configured to inhibit hydrogen bonding between the rings;
   (b) polymerizing the first peptide rings and the second peptide rings to produce a peptide nanotube polymer; and
   (c) deprotecting the protecting groups after the polymerizing,
   wherein the peptide nanotube polymer comprises alternating monomers of the first peptide ring and monomers of the second peptide ring covalently bonded to one another via a linker having a length of from 6 to 10 atoms,
   wherein the peptide rings are arranged such that an exterior surface of the peptide nanotube polymer corresponds to exteriors of the first and second peptide rings, and
   wherein said linker comprises at least one amide bond created from one of the primary amine functionalities and one of the carboxylic acid functionalities during the polymerization.

10. The method of claim 9, wherein the first peptide rings and/or the second peptide rings are functionalized with:
    (a) free amine;
    (b) free acid;
    (c) fluorophore/quencher pairs;
    (d) thiol;
    (e) insulating moiety;
    (f) alkyne;
    (g) photoisomerizable groups;
    (h) aryl- or vinyl-halide;
    (i) alkene;
    (j) azide;
    (k) conducting moiety;
    (l) multiply-bonded transition metals;
    (m) pyrene;
    (n) aryl- or vinyl-boronic acid; or
    (o) isocyanates.

* * * * *